(12) United States Patent
Mitchell et al.

(10) Patent No.: US 10,736,761 B2
(45) Date of Patent: Aug. 11, 2020

(54) METHOD OF MAKING A MEDICAL DEVICE USING ADDITIVE MANUFACTURING WITH A MASKING PLATE

(71) Applicant: Medtronic Vascular, Inc., Santa Rosa, CA (US)

(72) Inventors: James Mitchell, Windsor, CA (US); Syamala Rani Pulugurtha, Irvine, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 478 days.

(21) Appl. No.: 15/491,170

(22) Filed: Apr. 19, 2017

(65) Prior Publication Data

US 2018/0303643 A1 Oct. 25, 2018

(51) Int. Cl.
| | |
|---|---|
| *A61F 2/915* | (2013.01) |
| *B22F 7/02* | (2006.01) |
| *B22F 3/105* | (2006.01) |
| *B28B 1/00* | (2006.01) |
| *B33Y 10/00* | (2015.01) |
| *B22F 5/10* | (2006.01) |
| *B29C 64/153* | (2017.01) |

(Continued)

(52) U.S. Cl.
CPC ............ *A61F 2/915* (2013.01); *B22F 3/1055* (2013.01); *B22F 5/106* (2013.01); *B22F 7/02* (2013.01); *B28B 1/001* (2013.01); *B29C 64/153* (2017.08); *B33Y 10/00* (2014.12); *A61F 2002/91575* (2013.01); *A61F 2210/0076* (2013.01); *A61F 2240/001* (2013.01); *B22F 2998/10* (2013.01); *B29C 64/286* (2017.08); *B29K 2071/00* (2013.01); *B29L 2031/7534* (2013.01)

(58) Field of Classification Search
None
See application file for complete search history.

(56) References Cited

U.S. PATENT DOCUMENTS

| 8,353,952 B2 | 1/2013 | Thompson et al. | |
| 9,114,032 B1 * | 8/2015 | Pulugurtha | ............... C23F 1/02 |

(Continued)

OTHER PUBLICATIONS

Denney P., et al., "Triple Hopper Powder Feeder System for Variable Composition Laser Cladding", Laser Materials Processing, vol. 77, Oct. 24-28, 1993.

*Primary Examiner* — Keith Walker
*Assistant Examiner* — Stephani Hill
(74) *Attorney, Agent, or Firm* — Medler Ferro Woodhouse & Mills PLLC

(57) ABSTRACT

A medical device having a first portion, a second portion, and at least one connector connecting the first and second portion is formed using additive manufacturing. The method includes forming a plurality of layers of a first portion of the medical device, placing a first removable masking plate over the first portion with an opening of the masking plate aligned with a point of the first portion, forming at least one layer of a first connector on the first portion, wherein the first connector is formed in the opening of the removable masking plate, forming a plurality of layers of a second portion of the medical device, wherein a first layer of the plurality of layers of the second portion is formed partially on the first connector and partially on the removable masking plate, and removing the first removable masking plate.

23 Claims, 11 Drawing Sheets

(51) Int. Cl.
  *B29K 71/00*   (2006.01)
  *B29C 64/286*  (2017.01)
  *B29L 31/00*   (2006.01)

(56) References Cited

U.S. PATENT DOCUMENTS

| | | | |
|---|---|---|---|
| 10,295,041 B2 * | 5/2019 | Akanishi | F16H 55/30 |
| 2007/0061007 A1 | 3/2007 | Nolting | |
| 2008/0091267 A1 | 4/2008 | Stinson et al. | |
| 2008/0131479 A1 | 6/2008 | Weber et al. | |
| 2009/0250430 A1 * | 10/2009 | Zhang | B32B 38/10 216/36 |
| 2011/0067778 A1 | 3/2011 | Mitchell et al. | |
| 2011/0070357 A1 | 3/2011 | Mitchell et al. | |
| 2011/0070358 A1 | 3/2011 | Mauch et al. | |
| 2012/0067454 A1 | 3/2012 | Melder | |
| 2012/0067455 A1 | 3/2012 | Mitchell et al. | |
| 2012/0070562 A1 | 3/2012 | Avelar et al. | |
| 2012/0070563 A1 | 3/2012 | Mitchell et al. | |
| 2013/0331927 A1 | 12/2013 | Zheng et al. | |
| 2014/0277375 A1 | 9/2014 | Weier et al. | |
| 2015/0010422 A1 | 1/2015 | Nash | |
| 2015/0056321 A1 * | 2/2015 | Zhang | B29C 64/35 425/225 |
| 2017/0120331 A1 * | 5/2017 | Ishida | B29C 64/153 |
| 2018/0229426 A1 * | 8/2018 | Douroumis | B29C 64/209 |

* cited by examiner

METHOD OF MAKING A MEDICAL DEVICE USING ADDITIVE MANUFACTURING WITH A MASKING PLATE

FIELD OF THE INVENTION

The invention relates generally to methods of making medical devices, and more particularly to a method of making stents using additive manufacturing.

BACKGROUND OF THE INVENTION

A wide range of medical treatments exist that utilize medical devices such as stents or endoluminal prostheses. As used herein, the term "stent" is intended to cover medical devices that are adapted for temporary or permanent implantation within a body lumen, including both naturally occurring and artificially made lumens, such as without limitation: arteries, whether located within the coronary, mesentery, peripheral, or cerebral vasculature; veins; gastrointestinal tract; biliary tract; urethra; trachea; hepatic shunts; and fallopian tubes.

Accordingly, different stents have been developed, each providing a uniquely beneficial structure to modify the mechanics of the targeted lumen wall. For example, stent prostheses are known for implantation within body lumens to provide artificial radial support to the wall tissue, which forms the various lumens within the body, and often more specifically, for implantation within the blood vessels of the body.

Stents have been made by a variety of methods, including forming a wire into waveform and helically wrapping the waveform around a mandrel, removing material from a tubular cylinder such as by a laser to leave a stent (sometimes referred to as a tubular slotted stent or a laser cut stent), and forming individual cylindrical components and attaching adjacent cylindrical components to each other to form a tube. Such methods can be laborious, expensive, and time-consuming. It would be desirable to use additive manufacturing techniques, also known as rapid prototyping methods and three-dimensional printing, to make stents and other medical devices. However, additive manufacturing techniques may be limited in making certain shapes for medical devices, and particularly for certain shapes of stents. For example, and not by way of limitation, certain medical devices that are generally tubular, such as stents, may be formed by additive manufacturing by building the medical device vertically. In other words, the longitudinal axis of the medical device is perpendicular to the surface or substrate upon which the medical device is built. In additive manufacturing, layers of material for the medical device are built upon previous layers of the material. In certain medical devices, such as certain stents, it is desirable for a significant portion of a perimeter of a first portion of the device to not be connected to a second portion of the device. For example, and not by way of limitation, in a stent with a plurality of bands formed from struts and crowns, it is often desirable for only some of the crowns of a band to be connected to crowns of an adjacent band. However, when building such a stent vertically by additive manufacturing as described above, it is desirable for connectors to be built between most or all of the crowns of adjacent bands in order to provide a support for the following layer of material.

In a solution described in U.S. Pat. No. 9,114,032 assigned to Medtronic Vascular, Inc., incorporated by reference herein in its entirety, connectors are formed between all crowns of a stent by additive manufacturing. Some of the connectors are then removed by laser removal, chemical etching, or other methods. In particular embodiments, the connectors configured to be removed are formed from a different material than the connectors configured to remain. Then, the precursor stent is exposed to a chemical etchant that dissolves/removes the connectors configured to be removed without adversely affecting the stent components configured to remain. However, changing materials during additive manufacturing may complicate the process. Further, mechanical removal of connectors may be difficult if the connectors to be removed are the same as the connectors to remain.

Accordingly, it would be desirable to build a medical device such as a stent by additive manufacturing with only the desired connectors between portions of the medical device.

BRIEF SUMMARY OF THE INVENTION

Embodiments hereof relate to a method of making a medical device using additive manufacturing. In an embodiment, the medical device includes a plurality of portions disposed adjacent to each other and at least one connector connecting each portion to an adjacent portion. In the method, a plurality of layers of a first portion of the plurality of portions are formed by additive manufacturing. A removable masking plate is placed over the first portion. The removable masking plate includes at least one opening aligned with a point of the first portion. At least one layer of a first connector is formed on the first portion in the at least one opening of the removable masking plate. A plurality of layers of a second portion of the plurality of portions are formed. A first layer of the plurality of layers of the second portion is formed partially on the first connector and partially on the removable masking plate. The removable masking plate is then removed.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements.

Figure 1:
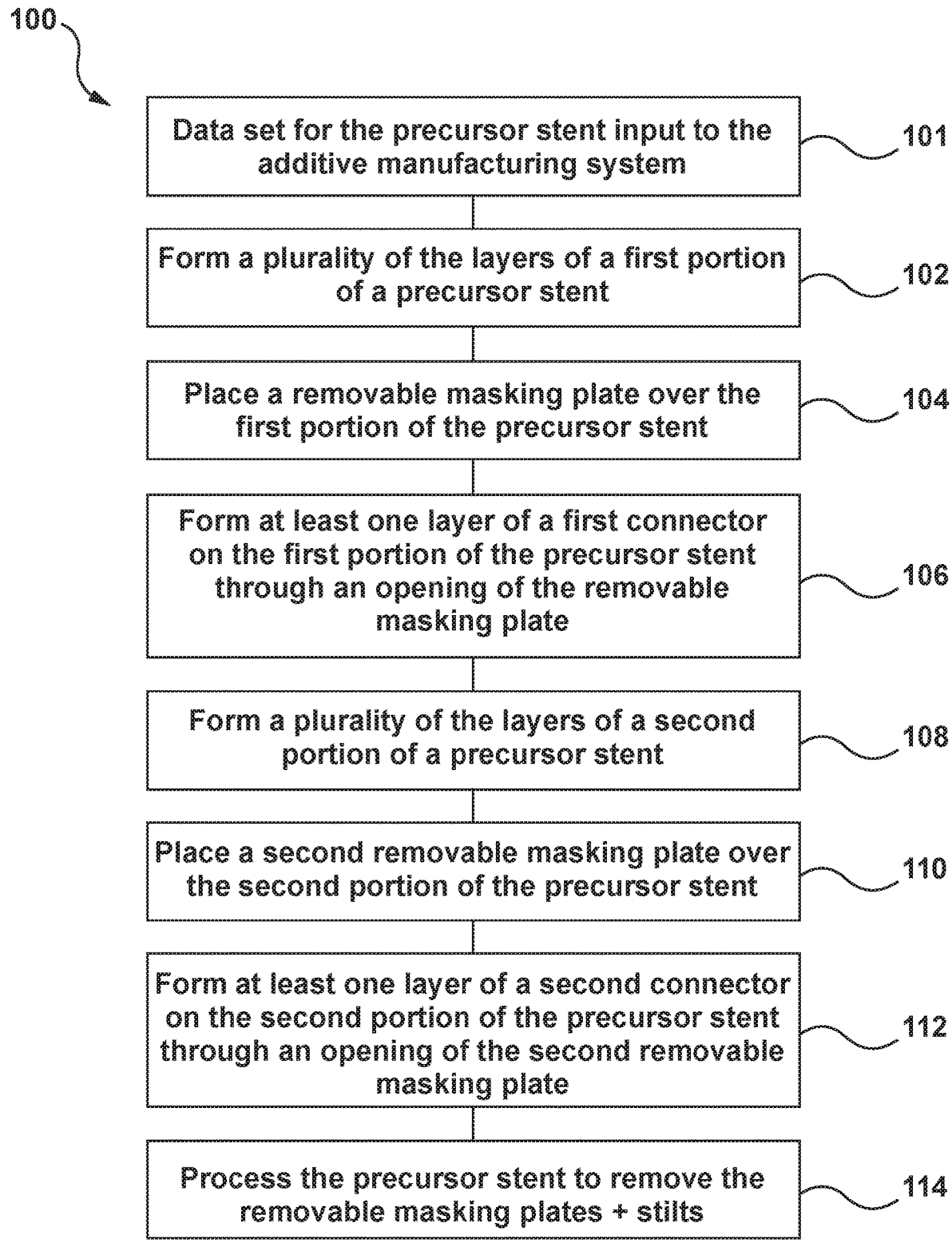
FIG. 1 is a flow chart showing steps in an embodiment of a method of making a medical device according to an embodiment hereof.

FIG. 1 is a flow chart showing an embodiment of a method 100 of making a medical device. The method as described with respect to FIG. 1 is a method for making a medical device using "additive manufacturing" or "three-dimensional printing" (3D printing) or "rapid prototyping". The terms "additive manufacturing", "three-dimensional printing", and "rapid prototyping" refer to a process of making a three-dimensional solid object of virtually any shape from a digital model. The desired object is achieved using an additive process, where successive layers of material are laid down in different shapes. The terms, as used herein, may refer to methods such as, but not limited to, selective laser melting (SLM), direct metal laser sintering (DMLS), selective laser sintering (SLS), fused deposition modeling (FDM), and stereolithography (SLA). Further, any type of additive manufacturing system that can print the materials described herein may be used.

Figure 2:
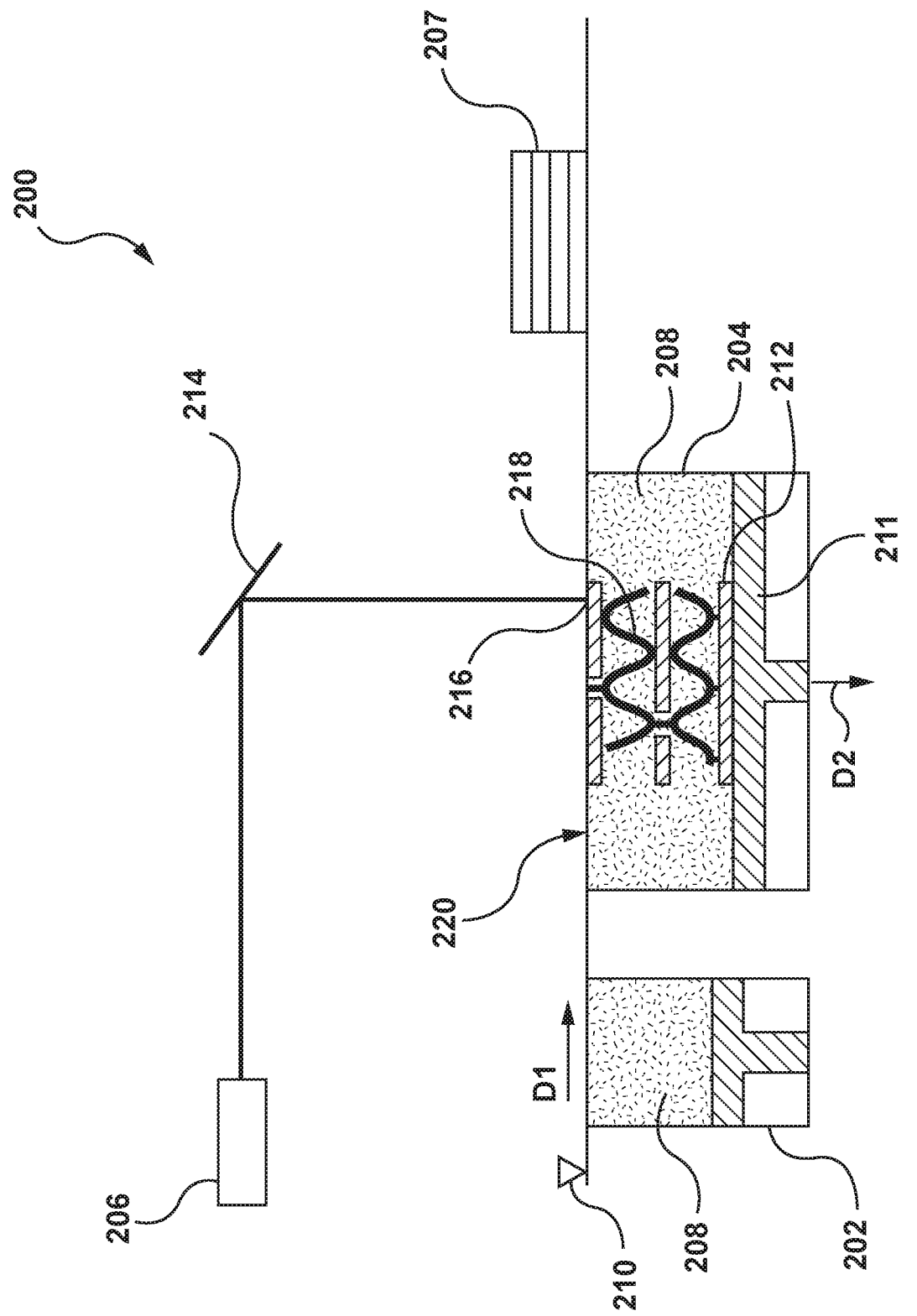
FIG. 2 is an illustration of an additive manufacturing system for use with the method of FIG. 1.

Accordingly, FIG. 2 shows a simplified exemplary embodiment of an additive manufacturing system 200 suitable for use in the method of FIG. 1. The additive manufacturing system 200 of FIG. 2 includes a powder delivery system 202, a build space 204, an energy source 206, and a removable masking plate dispenser 207. In general, powder material 208 from the powder delivery system 202 is spread by a blade 210 on a surface 220 in a direction D1 such that a thin layer of the powder material 208 is deposited over a substrate 212 disposed on a platform 211 of the build space 204. The energy source 206 (such as a laser, electron beam, or similar source) is targeted by a mirror 214 to selectively fuse the powder material 208 at a fuse zone or laser focal zone 216 in a desired pattern. The platform 211 is retracted in a direction D2 and successive layers of distributed powder material 208 are in the build space 204 and selectively fused until the desired object 218 is formed. Stated another way, the additive manufacturing system 200 forms objects by successively layering the powder material 208 and then fusing particles of the powder material 208 together and to the adjacent layer with the energy source 206. While FIG. 2 shows the platform 211 and the substrate 212 partially retracted after several layers of the powder material 208 have been fused, the substrate 212 starts the process adjacent the surface 220. The powder-bed additive manufacturing system 200 of FIG. 2 is one possible embodiment of an additive manufacturing system suitable for the method described herein and is not meant to be limiting. Other additive manufacturing systems are possible including, but not limited to a powder-fed, funnel-fed, or conduit-fed additive manufacturing systems.

Thus, the object 218 (in this embodiment a precursor stent as described below), is built layer-by-layer. However, in order for a subsequent layer of powder material 208 to be fused, it must be supported. Typically, support is provided by the preceding layer of fused material as the object is formed vertically. However, with certain medical devices, such as certain stents, it is desirable for a significant portion of a perimeter of a first band (portion) of the stent to not be connected to a second band (portion) of the stent, as will be described in greater detail below. However, in many embodiments, these portions cannot be excluded during additive manufacturing because the following layers need support upon which to build. Thus, when building such a stent vertically by additive manufacturing, it may be necessary for connectors to be built between most or all of the crowns of adjacent bands in order to provide a support for the following layer of material. As noted above, some of the connectors are not desirable in the final stent and therefore must be removed.

Therefore, in accordance with embodiments hereof and as described in more detail below, a removable masking plate is disposed between adjacent bands (portions) of the precursor stent to mask the areas that are not to be connected between the adjacent bands. The removable masking plate provides the underlying support for the following layers of material. The method of FIG. 1 using the additive manufacturing system 200 of FIG. 2 will now be described in more detail.

Figure 10:
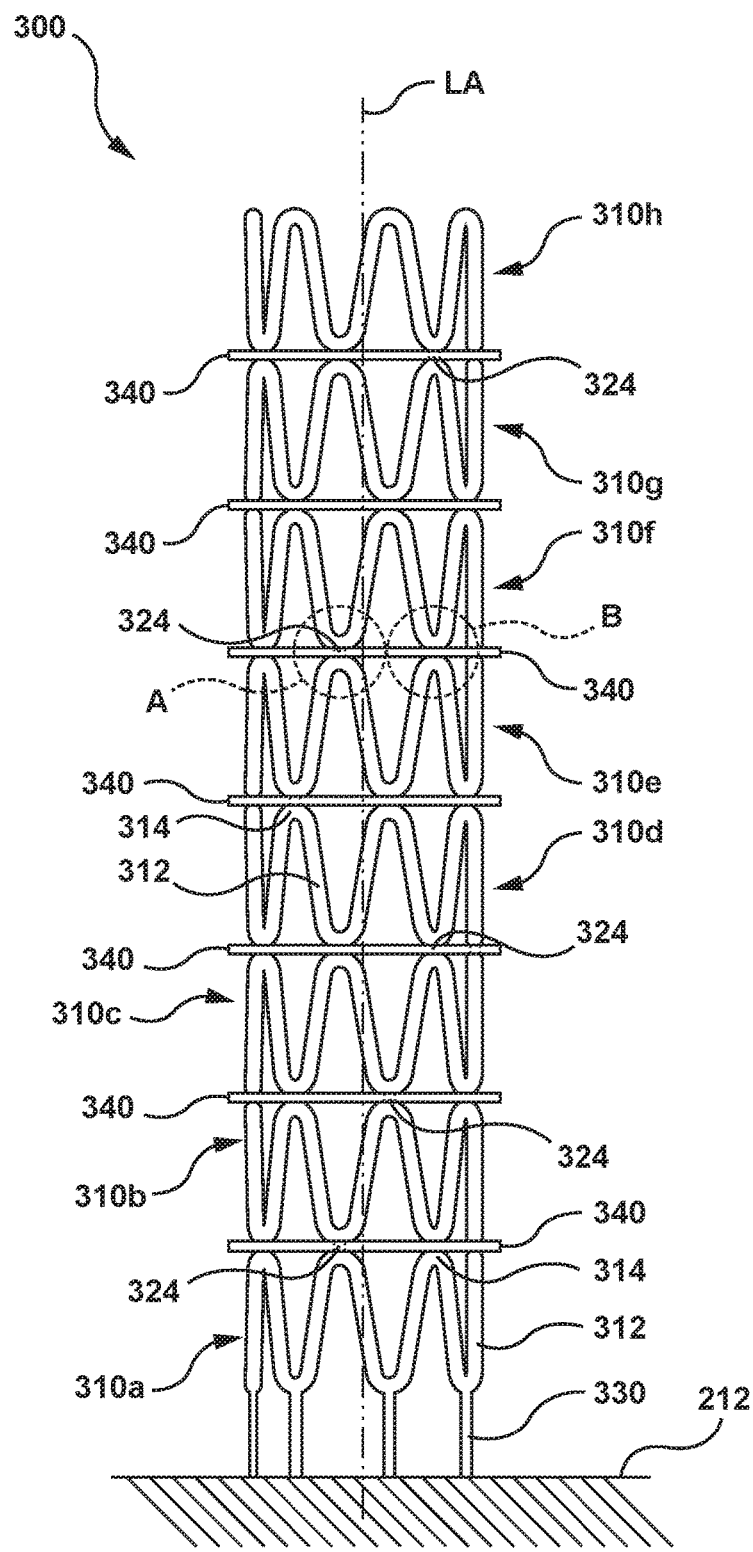
FIG. 10 is a schematic side illustration of an embodiment of the precursor stent made in accordance with the method of FIG. 1.

In an embodiment, in step 101 of the method 100 of FIG. 1, the additive manufacturing system 200 receives a dataset corresponding to a precursor stent 300, shown in FIG. 10. In particular, the dataset is information regarding the characteristics of the precursor stent 300 from which the additive manufacturing system 200 can form the precursor stent 300. For example, the sizes and locations of parts of the precursor stent 300 may be part of the dataset such that the additive manufacturing system 200 can form the precursor stent 300. For example, and not by way of limitation, the dataset may be a 3D printable file such as an STL file. STL (STereoLithography) is a file format native to the stereolithography CAD software created by 3D Systems. STL is also known as Standard Tessellation Language. This file format is supported by many software packages for use in additive manufacturing.

Figure 3:
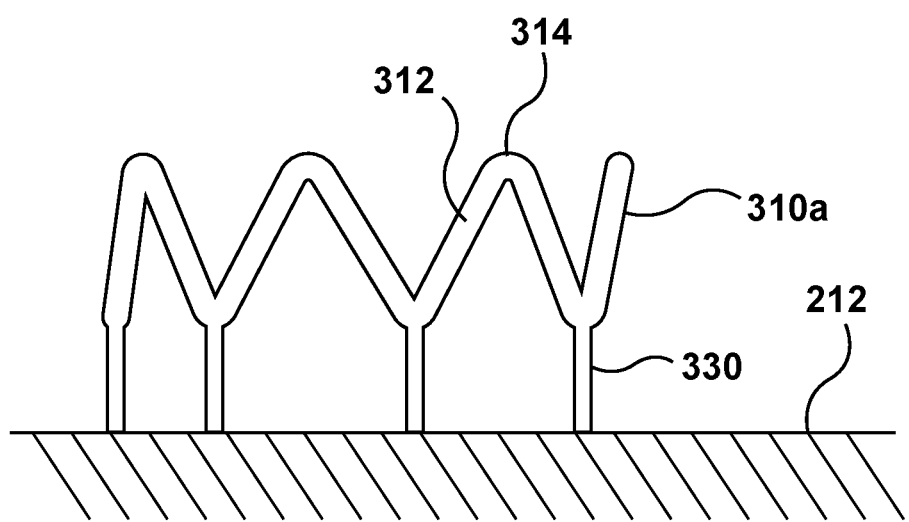
FIG. 3 is a schematic illustration of a first band (portion) of a precursor stent made in a step of the method of FIG. 1.

Step 102 of the method 100 of FIG. 1 is for the additive manufacturing system 200 to form a plurality of layers of a first portion or band 310a of the precursor stent 300, as shown in FIG. 3. In step 102, the additive manufacturing system 200 lays down successive layers of the powder material 208 of the desired material to build the first band 310a from a series of cross sections. After each layer of the powder material 208 is laid down, the energy source 206 (such as a laser, electron beam, or similar source) selectively fuses the layer of the powder material 208 together and to the adjacent (previous) layer. This is repeated for the desired number of layers to form the first band 310a of the precursor stent 300. In the embodiment of FIG. 3, the first band 310a is formed vertically on the substrate 212 and a plurality of stilts or connectors 330, as described in U.S. Pat. No. 9,114,032. However, this is not meant to be limiting, and first band 310a may be built directly on the substrate 212 or on another substance disposed between the substrate and the first band 310a, such as, but not limited to a removable masking plate described in greater detail below. In an embodiment, the first band 310a is a ring-shaped waveform formed from a plurality of struts 312 connected together by bends or crowns 314. The powder material 208 is the material desired for the finished stent (FIG. 14) as explained in more detail below.

Figure 4:
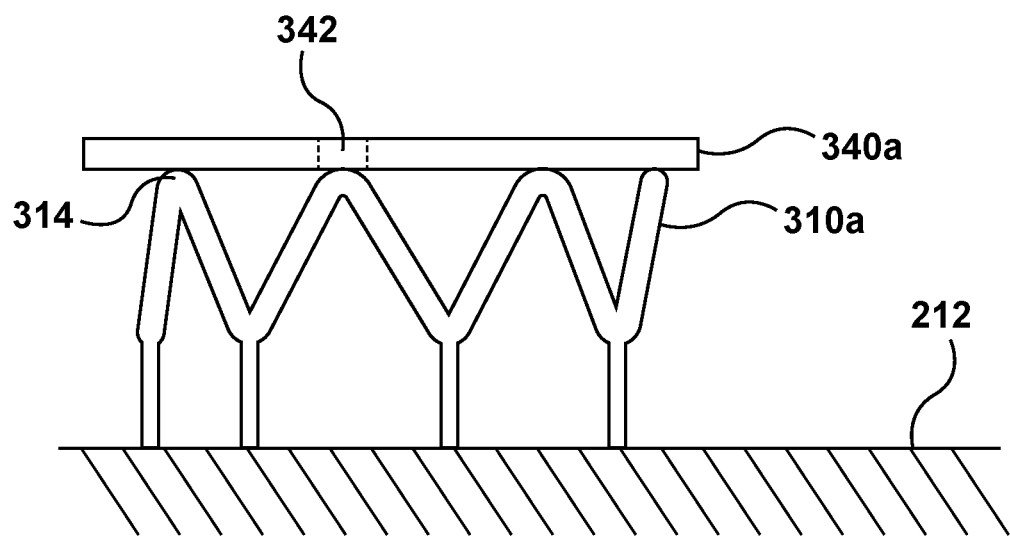
FIG. 4 is a schematic illustration of a removable masking plate disposed on the first band (portion) in a step of the method of FIG. 1.
Figure 5:
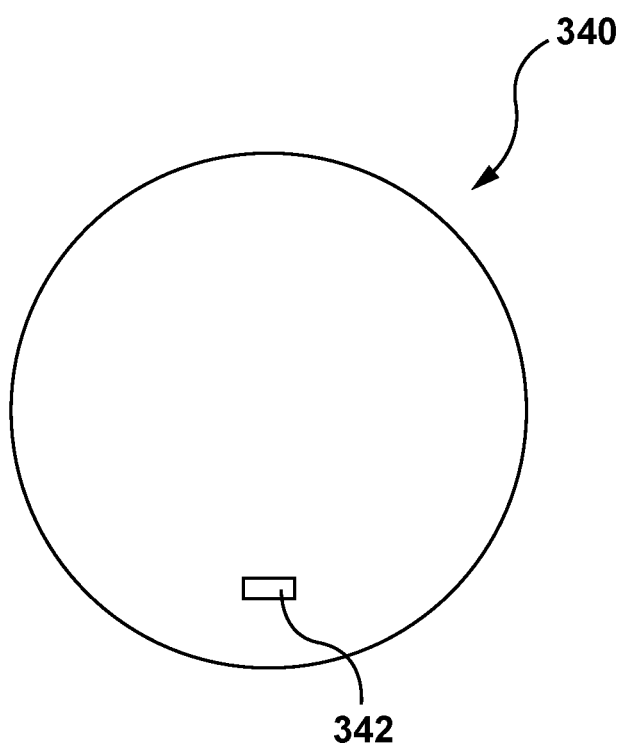
FIG. 5 is a close-up schematic illustration of the masking plate of FIG. 4.

Once the first band 310a is formed, in step 104 a first removable masking plate 340a is placed over the first band 310a of the precursor stent 300, as shown in FIG. 4. An embodiment of a removable masking plate 340 is shown in greater detail in FIG. 5. Each removable masking plate 340 includes at least one opening 342. The removable masking plate 340 is configured such that when the removable masking plate 340 is placed over a band 310, each opening 342 is aligned over a crown 314 of the band 310. Thus, as shown in FIG. 4, the first masking plate 340a is placed over the first band 310a with the opening 342 aligned over a crown 314 of the first band 310a. For the crowns 314 of the first band 310a that are not aligned with the opening 342 of the first masking plate 340a, a solid portion of the solid masking plate 340a is disposed over the crowns 314.

The removable masking plate 340 may be in the form of a sheet, foil, tape, or other suitable form for use herein. The particular dimensions of the removable masking plate 340, such as length, width, thickness and/or diameter may be determined by the particular stent design. For example, the desired length of the connectors 324 between each band 310 may determine the thickness of the removable masking plate 340. Similarly, the diameter of the bands 310 may determine the diameter of the removable masking plates 340. In the embodiment of FIGS. 4-12, each removable masking plate 340 includes one opening 342. However, this is not meant to limit the design or method, and each masking plate 340 may include more than one opening 342. Moreover, each removable masking plate 340 may include a different number of openings 342, in different locations, and in any combination as desired. Further, in the embodiment shown in FIG. 4, the opening 342 is generally rectangular. However, this is not meant to limit the design or method, and the opening(s) 342 may be of any shape or size depending on the shape and size desired for the resulting connectors. Further, different openings 342 of different removable masking plates 340, or different openings 342 of a removable masking plate 340 with multiple openings 342, may have different shapes and/or sizes, resulting in connectors 324 of a stent having a variety of cross-sectional shapes and sizes.

In the embodiment of the additive manufacturing system 200 of FIG. 2, after the first band 310a is formed, the first removable masking plate 340a is dispensed from the removable masking plate dispenser 207. The first removable masking plate 340a may be automatically positioned over the first band 310a. In other embodiments, each removable masking plate 340 may be dispensed from other devices. Further, each removable masking plate 340 may be positioned either automatically, semi-automatically, or manually over the formed band 310. While the removable masking plate 340 is shown in the embodiment as a disc, this is not meant to limit the design and the shape of each removable masking plate 340 may be of any shape suitable for the intended application. For example, and not by way of limitation, each removable masking plate 340 may be ring or donut shaped with a central opening in addition to the opening 342.

Figure 6:
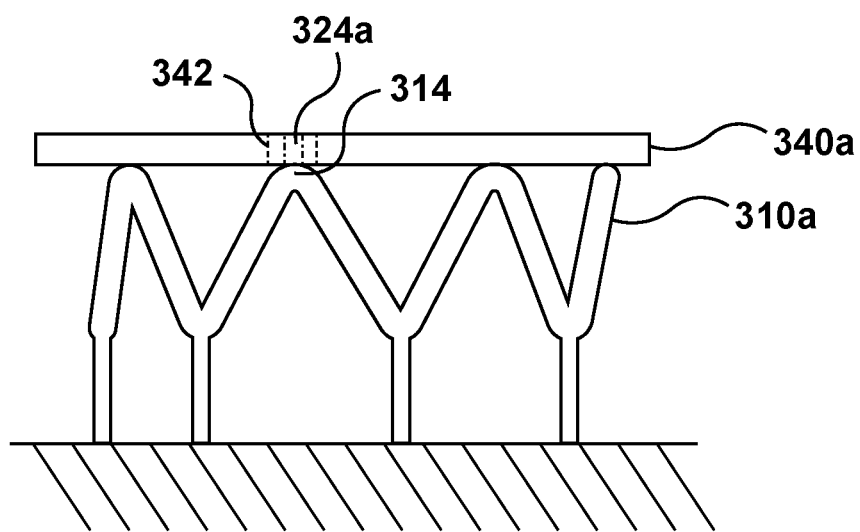
FIG. 6 is a schematic illustration of a connector formed through an opening of the removable masking plate in a step of the method of FIG. 1.

In the next step 106, the additive manufacturing system 200 lays down at least one layer of the powder material 208 of the desired material to build the first connector 324a, as shown in FIG. 6. More specifically, the powder material 208 is spread over the first removable masking plate 340a. Some of the powder material 208 will fall into the opening 342 of the first removable masking plate 340a and rest on one of the crowns 314 of the first band 310a. The energy source 206 is aligned with the opening 342 in the removable masking plate 340a such that the laser focal zone 216 is located where the powder material 208 is disposed in the opening 342. The energy source 206 fuses the particles of the powder material 208 disposed in the opening 342 to each other and to the previous layer. This step is repeated for as many layers as desired to form the first connector 324a on a corresponding crown 314 of the first band 310a through the opening 342 of the first removable masking plate 340a.

Figure 7:
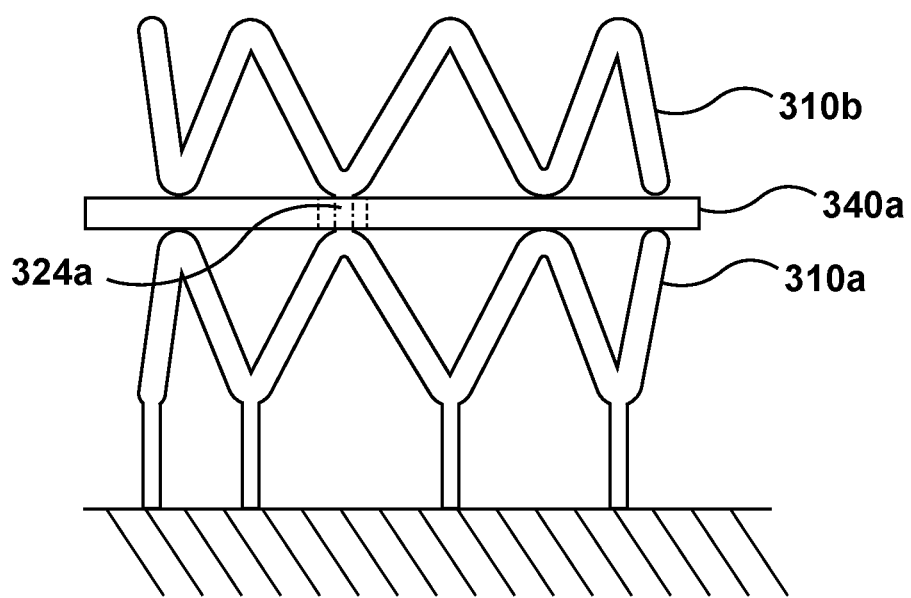
FIG. 7 is a schematic illustration of a second band (portion) formed on the first connector and the removable masking plate in a step of the method of FIG. 1.

Once the first connector 324a is formed through the opening 342 of the first masking plate 340a, in the following step 108 the additive manufacturing system 200 lays down successive layers of the powder 208 to build the second band 310b from a series of cross sections, as shown in FIG. 7. More precisely, the powder material 208 is spread over the first removable masking plate 340a such that some of the powder material 208 is deposited over the first connector 324a at the opening 342 and some of the powder material 208 is deposited on the first removable masking plate 340a. The energy source 206 then fuses the particles of the powder material 208 to each other in the desired pattern. At the location of the first opening 342, the powder material of the first layer of the second band 310b is fused to the first connector 324a. At locations other than the first opening 340, the first removable masking plate 340a acts as a substrate to support the first layer of the second band 310b. After the first layer of the second band 310b is formed, successive layers of the powder material 208 are laid down and fused to form the remainder of the second band 310b.

Figure 8:
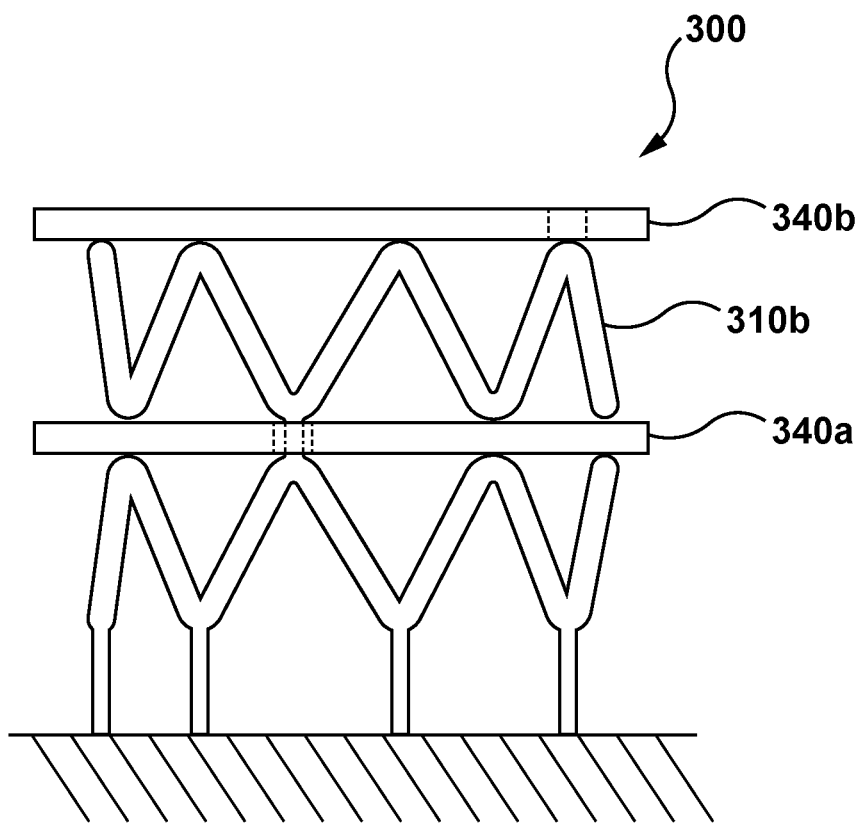
FIG. 8 is a schematic illustration of a second removable masking plate disposed on the second band (portion) in a step of the method of FIG. 1.

Once the second band 310b is formed, in step 110 a second removable masking plate 340b is placed over the second band 310b of the precursor stent 300, as shown in FIG. 8. The method of placement of the second removable masking plate 340b is similar to the method of placement of the first removable masking plate 340a, described previously.

Figure 9:
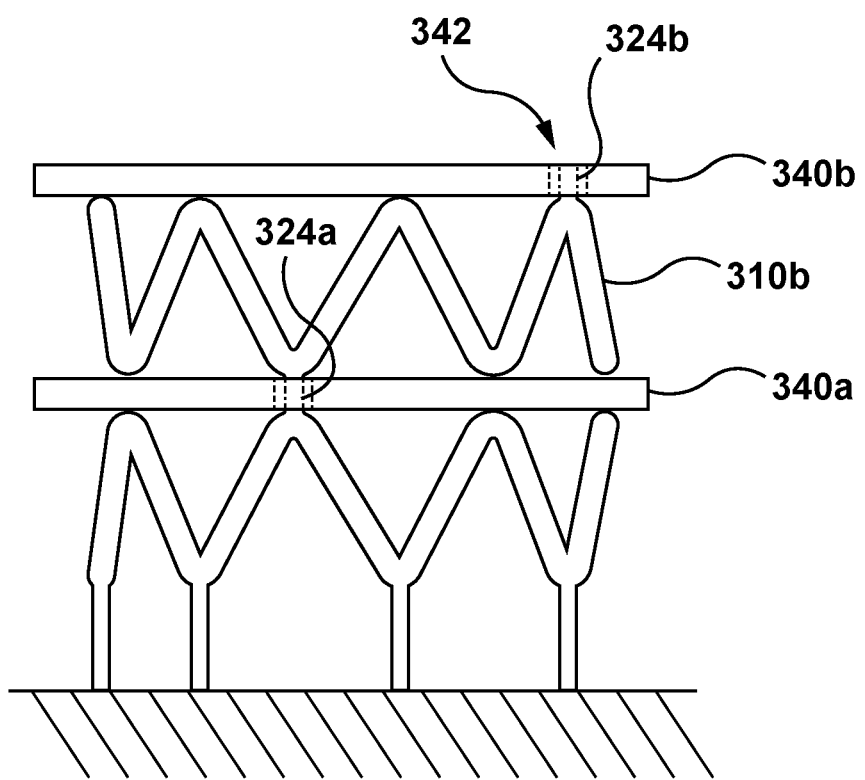
FIG. 9 is a schematic illustration of a connector formed through an opening of the second removable masking plate in a step of the method of FIG. 1

In the next step 112, the additive manufacturing system 200 lays down at least one layer of the powder material 208 of the desired material to build the second connector 324b, as shown in FIG. 9. More specifically, the powder material 208 is spread over the second removable masking plate 340b. Some of the powder material 208 will fall into the opening 342 of the second removable masking plate 340b and rest on one of the crowns 314 of the second band 310b. The energy source 206 is aligned with the opening 342 in the second removable masking plate 340b such that the laser focal zone 216 is located where the powder material 208 is disposed in the opening 342. The energy source 206 fuses the particles of the powder material 208 disposed in the opening 342 to each other and to the previous layer. This step is repeated for as many layers as desired to form the second connector 324b on a corresponding crown 314 of the second band 310b through the opening 342 of the second removable masking plate 340b.

The steps of forming a band 310 on a removable masking plate 340, placing another removable masking plate 340 thereon, and forming a connector 324 therethrough may be repeated until the desired precursor stent 300 is achieved.

Figure 11:
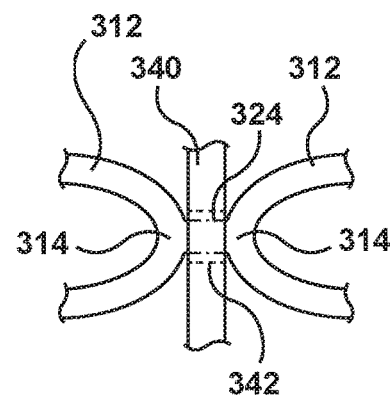
FIG. 11 is a close-up schematic illustration taken at area "A" of FIG. 10, showing the connector between crowns of adjacent bands and a portion of a masking plate between adjacent bands of the precursor stent.
Figure 12:
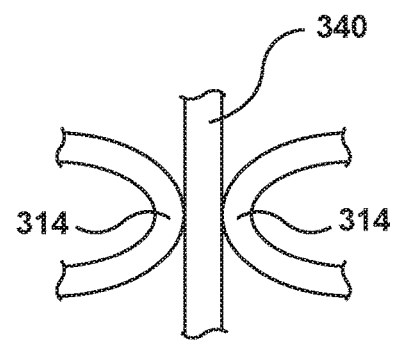
FIG. 12 is a close-up schematic illustration taken at area "B" of FIG. 10 showing a portion of the masking plate between crowns of adjacent bands of the precursor stent.

FIGS. 10-12 show an embodiment of the precursor stent 300 additively manufactured by the steps 102-112 of the method 100. The precursor stent 300 is built vertically on the substrate 212. The precursor stent 300 includes the plurality of bands 310. In the embodiment of FIG. 10, the precursor stent 300 includes eight bands 310a-310h, however, more or fewer bands 310 may be utilized. Each band (portion) 310 is disposed adjacent to another band (portion) 310 along a longitudinal axis LA to form a tube or cylinder. As described previously, each band 310 is formed from a plurality of struts 312 connected together by crowns 314. Further, one set of crowns 314 of the adjacent bands 310 are connected to each other by a connector 324. All other sets of crowns 314 of the adjacent bands 310 are separated by the removable masking plate 340, as shown in FIG. 10 and in greater detail in FIGS. 11-12. In particular, FIG. 11 is a close-up view of area "A" of FIG. 10 and illustrates a connector 324 extending through an opening 342 in a removable masking plate 340 to connect crowns 314 of adjacent bands 310. FIG. 12 shows a close-up view of area "B" of FIG. 10 and illustrates crowns 314 of adjacent bands 310 separated by a removable masking plate 340 at a location without an opening 342 in the removable masking plate 340. Further, the first band 310a may be separated from the substrate 212 by the stilts 330, as shown in FIG. 10. In other embodiments, the first band 310a may be built directly on the substrate 212 or may be built on a removable plate without any openings. If the stilts 330 are used, the stilts 330 may be configured to be removable from the precursor stent 300 such that the first band 310a is not damaged when separating the precursor stent 300 from the substrate 212.

As explained above, each crown 314 of a band 310 is connected to a corresponding crown 314 of an adjacent band 310 by a connector 324 or separated therefrom by a removable masking plate 340. The crowns 314 of a band 310 desired to be independent of or not connected to the corresponding crown 314 of an adjacent band 310 are therefore separated by one of the removable masking plates 340. As further explained above, each removable masking plate 340 is needed to support the following band 310 of the precursor stent 300. However, the removable masking plates 340 are not desired as part of the finished stent. Accordingly, step 114 of the method 100 of FIG. 1 is to process the precursor stent 300 to remove the removable masking plates 340 between adjacent bands 310. The processing step 114 to remove the removable masking plates 340 may be accomplished by exposing the precursor stent 300 to a condition or material that removes the removable masking plates 340 without adversely affecting the bands 310 and the connectors 324. Generally, the removable masking plates 340 are formed from a different material than the bands 310 and the connectors 324 such that the process of step 114 removes the removable masking plates 340 without adversely affecting the bands 310 and the connectors 324. For example, and not by way of limitation, step 114 may remove the removable masking plates 340 by physical methods, chemical reaction/etching, wet chemical dissolution, solubilization, sublimation, or melting.

For example, in one non-limiting example, the bands 310 and the connectors 324 may be formed of materials commonly used in a stent such as stainless steel (e.g. 316SS), cobalt-chromium alloys (e.g. cobalt-nickel-chromium alloys (MP35N, MP20N, MP35NLT), chromium-nickel-tungsten-cobalt alloys (L605)), or nickel-titanium alloys. The removable masking plates 340 may be made of a brittle material, such as, but not limited to, a ceramic material. The removable masking plates 340 may be removed by physical methods such as shattering the brittle ceramic material using a hammer, tweezers, dropping-off, etc. without damaging the more ductile (i.e., less brittle) bands 310 and connectors 324.

In another non-limiting example, the bands 310 and the connectors 324 may be formed of materials commonly used in a stent such as stainless steel (e.g. 316SS), cobalt-chromium alloys (e.g. cobalt-nickel-chromium alloys (MP35N, MP20N, MP35NLT), chromium-nickel-tungsten-cobalt alloys (L605)), or nickel-titanium alloys. The removable masking plates 340 may be made from aluminum or an aluminum alloy (such as an aluminum sheet). The aluminum will be preferentially etched by sodium hydroxide (NaOH) such that immersing the precursor stent 300 in NaOH will remove the aluminum masking plates 340 while leaving the bands 310 and the connectors 324 unharmed.

In another non-limiting example, the removable masking plates 340 may be a magnesium sheet and the bands 310 and the connectors 324 may be formed of materials commonly used in a stent such as stainless steel (e.g. 316SS) or cobalt-chromium alloys (e.g. cobalt-nickel-chromium alloys (MP35N, MP20N, MP35NLT), chromium-nickel-tungsten-cobalt alloys (L605)). Immersing the precursor stent 300 in an acidic solution will lead to preferential removal of the magnesium masking plates 340 while leaving the bands 310 and the connectors 324 unharmed. In another example, a potential (voltage) can be applied to the precursor stent 300 to promote and/or hasten the reaction. In the example above, the magnesium masking plates 340 can be preferentially removed by immersing the precursor stent 300 in water (or an acidic solution) and applying a positive potential to the precursor stent 300, thereby removing the magnesium masking plates 340.

In another non-limiting example, the precursor stent 300 is exposed to a hot oxidizing environment to consume the removable masking plates 340. For example, the removable masking plates 340 of the precursor stent 300 may each be a magnesium sheet and the bands 310 and the connectors 324 of the precursor stent 300 may be formed of materials commonly used in a stent such as stainless steel (e.g. 316SS) or cobalt-chromium alloys (e.g. cobalt-nickel-chromium alloys (MP35N, MP20N, MP35NLT), chromium-nickel-tungsten-cobalt alloys (L605)). Exposing the precursor stent 300 to oxygen above the autoignition temperature (approximately 473° C.) of magnesium will cause the magnesium masking plates 340 to rapidly oxidize without adversely affecting the bands 310 and the connectors 324.

In another non-limiting example, the removable masking plates 340 may be made of polyetherimide, and the bands 310 and the connectors 324 may be formed of materials commonly used in a stent such as stainless steel (e.g. 316SS), cobalt-chromium alloys (e.g. cobalt-nickel-chromium alloys (MP35N, MP20N, MP35NLT), chromium-nickel-tungsten-cobalt alloys (L605)), or nickel-titanium alloys. Immersing the precursor stent 300 in chloroform will dissolve the polymer masking plates 340 without adversely affecting the bands 310 and the connectors 324.

In another non-limiting example, the precursor stent 300 may be formed with zinc sheets as the removable masking plates 340, and the bands 310 and the connectors 324 may be formed of materials commonly used in a stent such as stainless steel (e.g. 316SS), Cobalt-chromium alloys (e.g. cobalt-nickel-chromium alloys (MP35N, MP20N, MP35NLT), chromium-nickel-tungsten-cobalt alloys (L605)), or nickel-titanium alloys. Exposing the precursor stent 300 to temperatures between the melt temperature (about 420° C.) and the boiling temperature (about 907° C.) for zinc, and thus below the melt temperature for the material of the bands 310 and the connectors 340, will cause the zinc masking plates 340 to melt without adversely affecting the bands 310 and the connectors 324.

In another non-limiting example, the precursor stent 300 may be formed with a zinc sheet as the removable masking plates 340, and the bands 310 and the connectors 324 may be formed of materials commonly used in a stent such as stainless steel (e.g. 316DD), Cobalt-chromium alloys (e.g. cobalt-nickel-chromium alloys (MP35N, MP20N, MP35NLT), chromium-nickel-tungsten-cobalt alloys (L605)), or nickel-titanium alloys. Exposing the precursor stent 300 to temperature and pressure conditions in excess of the boiling point for zinc, while below the boiling point for the material of the bands 310 and the connectors 324, will sublimate the zinc removable masking plates 340 without adversely affecting the bands 310 and the connectors 324. In a particular example, heating the precursor stent 300 in a vacuum will reduce the energy required to sublimate the zinc removable masking plates 340.

The above examples are not comprehensive. Further non-limiting examples of materials used for the bands 310, the connectors 324, and the removable masking plates 340, and examples of processes to remove the removable masking plates 340 are provided in the chart below. These examples are not exhaustive and other materials and processes may be used to remove the masking plates 340 without adversely affecting the bands 310 and connectors 324.

| Process/Etchant | Bands 310/connectors 324 | Masking plates 340 |
| --- | --- | --- |
| Neutral to acidic solution | cobalt-chromium alloys (e.g., cobalt-nickel-chromium alloys (MP35N, MP20N, MP35NLT), chromium-nickel-tungsten-cobalt alloys (L605)), nickel-titanium alloys, molybdenum bearing stainless steel alloys (316SS) | iron, zinc, magnesium |
| Nitric acid | Cobalt-chromium alloys (e.g., cobalt-nickel-chromium alloys (MP35N, MP20N, MP35NLT), chromium-nickel-tungsten-cobalt alloys (L605)), nickel-titanium alloys, molybdenum bearing stainless steel alloys (316SS) | lead, silver, polyether ether ketone (PEEK) |
| Sulfuric Acid | Cobalt-chromium alloys (e.g., cobalt-nickel-chromium alloys (MP35N, MP20N, MP35NLT), chromium-nickel-tungsten-cobalt alloys (L605)), nickel-titanium alloys, molybdenum bearing stainless steel alloys (316SS) | Copper, copper coated calcium carbonate, Polyether ether ketone (PEEK) |
| Basic solutions (NaOH, NH$_3$, etc.) | Cobalt-chromium alloys (e.g., cobalt-nickel-chromium alloys (MP35N, MP20N, MP35NLT), chromium-nickel-tungsten-cobalt alloys (L605)), nickel-titanium alloys, molybdenum bearing stainless steel alloys (316SS) | Aluminum, aluminum oxide |
| Chloroform, Methylethylketone, Methylene Chloride, Trichloroethane, Trichloroethylene | Cobalt-chromium alloys (e.g., cobalt-nickel-chromium alloys (MP35N, MP20N, MP35NLT), chromium-nickel-tungsten-cobalt alloys (L605)), nickel-titanium alloys, molybdenum bearing stainless steel alloys (316SS) | Polyetherimide |
| Acidic solutions | Cobalt-chromium alloys (e.g., cobalt-nickel-chromium alloys (MP35N, MP20N, MP35NLT), chromium-nickel-tungsten-cobalt alloys (L605)) nickel-titanium alloys molybdenum bearing stainless steel alloys (316SS) | Calcium carbonate, hydroxyapatite |
| Melting - (Temperature greater than the masking plate material's melt point and less than stent material melt point) | Cobalt-chromium alloys (e.g., cobalt-nickel-chromium alloys (MP35N, MP20N, MP35NLT), chromium-nickel-tungsten-cobalt alloys (L605)) nickel-titanium alloys molybdenum bearing stainless steel alloys (316SS) | tin, lead, magnesium, zinc, aluminum, Polyether ether ketone (PEEK), polyetherimide |

-continued

| Process/Etchant | Bands 310/connectors 324 | Masking plates 340 |
| --- | --- | --- |
| Sublimation (Temperature in excess of vapor equilibrium point for a given pressure) | Cobalt-chromium alloys (e.g., cobalt-nickel-chromium alloys (MP35N, MP20N, MP35NLT), chromium-nickel-tungsten-cobalt alloys (L605)) nickel-titanium alloys molybdenum bearing stainless steel alloys (316SS) | tin, lead, magnesium, zinc, aluminum |
| Xenon difluoride ($XeF_2$) | Cobalt-chromium alloys (e.g., cobalt-nickel-chromium alloys (MP35N, MP20N, MP35NLT), chromium-nickel-tungsten-cobalt alloys (L605)), molybdenum bearing stainless steel alloys (316SS) | tantalum, molybdenum, tungsten, titanium, silicon carbide (SiC) |
| High temperature with oxygen, or aqueous or acidic solution with positive potential applied | Cobalt-chromium alloys (e.g., cobalt-nickel-chromium alloys (MP35N, MP20N, MP35NLT), chromium-nickel-tungsten-cobalt alloys (L605)), molybdenum bearing stainless steel alloys (316SS) | magnesium |
| Chlorine or fluorine plasma | Cobalt-chromium alloys (e.g., cobalt-nickel-chromium alloys (MP35N, MP20N, MP35NLT), chromium-nickel-tungsten-cobalt alloys (L605)), molybdenum bearing stainless steel alloys (316SS) | titanium diboride (TiB2), zirconium diboride |
| hydrogen fluoride (HF) | Cobalt-chromium alloys (e.g., cobalt-nickel-chromium alloys (MP35N, MP20N, MP35NLT), chromium-nickel-tungsten-cobalt alloys (L605)), molybdenum bearing stainless steel alloys (316SS) | Yytria stabilized zirconia |
| Chlorine trifluoride gas, or hydrogen fluoride (HF) and nitric acid | Cobalt-chromium alloys (e.g., cobalt-nickel-chromium alloys (MP35N, MP20N, MP35NLT), chromium-nickel-tungsten-cobalt alloys (L605)), molybdenum bearing stainless steel alloys (316SS) | silicon carbide (SiC) |
| Thermal decomposition (Temperature > thermal decomposition temperature of masking plates) | Cobalt-chromium alloys (e.g., cobalt-nickel-chromium alloys (MP35N, MP20N, MP35NLT), chromium-nickel-tungsten-cobalt alloys (L605)), nickel-titanium alloys, molybdenum bearing stainless steel alloys (316SS) | Polyether ether ketone (PEEK), polyetherimide |

Figure 13:
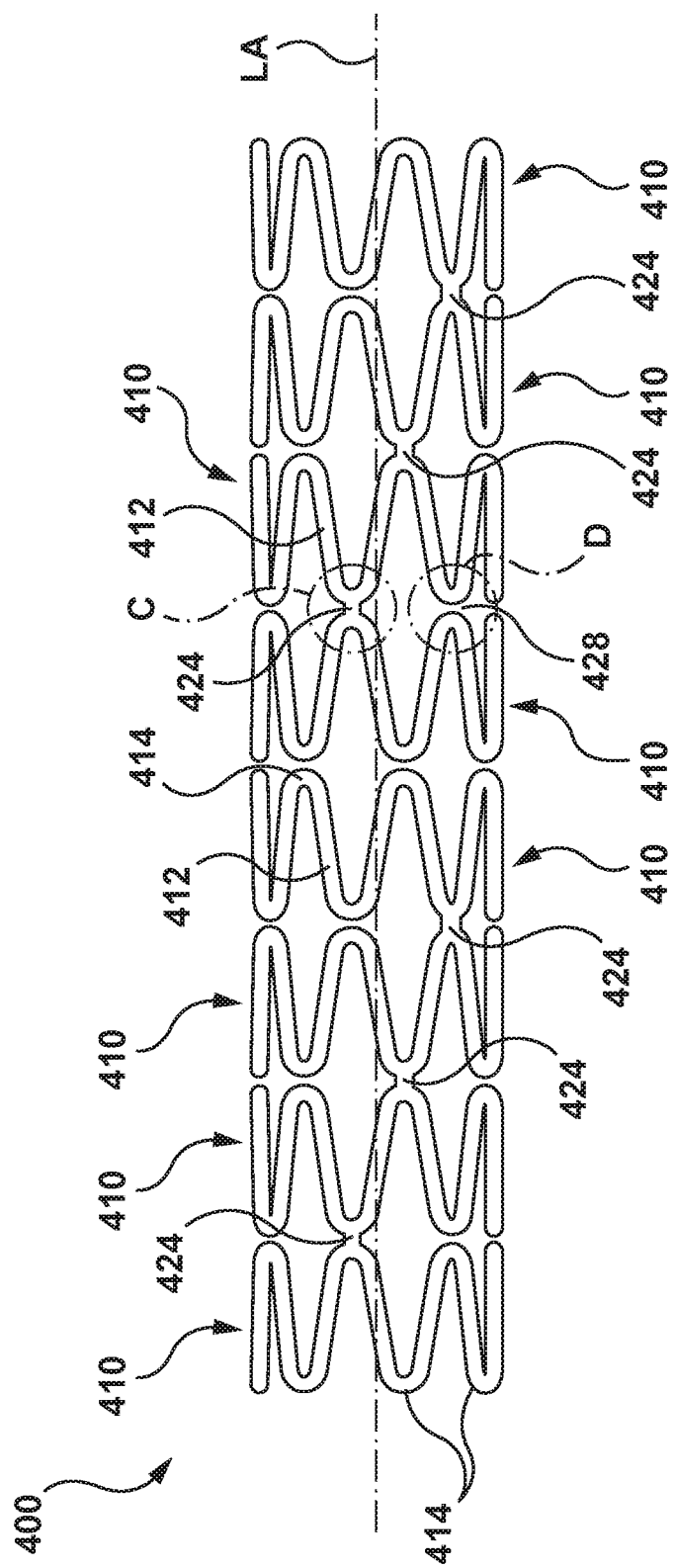
FIG. 13 is a schematic side illustration of an embodiment of a stent made using the method of FIG. 1.
Figure 15:
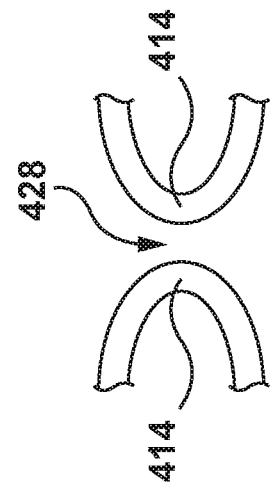
FIG. 15 is a close-up schematic illustration of an embodiment of a gap between crowns of adjacent bands of the stent of FIG. 13 taken at area "D" of FIG. 14.
Figure 14:
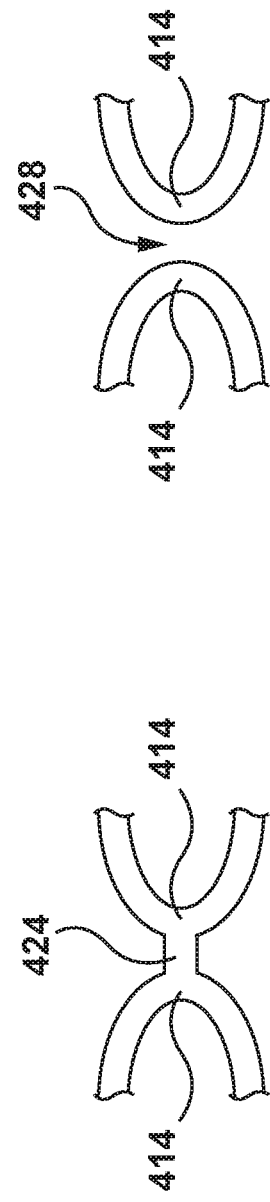
FIG. 14 is a close-up schematic illustration of an embodiment of a connector between crowns of adjacent bands of the stent of FIG. 13 taken at area "C" of FIG. 14.

With method 100 completed and the removable masking plates 340 removed, the precursor stent 300 has been transformed to the stent 400 shown in FIGS. 14-16. The stent 400 includes a plurality of ring-shaped elements or cylindrical elements or portions or bands 410. In the embodiment of FIG. 13, the stent 400 includes eight bands 410 corresponding to the eight bands 310 of the precursor stent 300. However, more or fewer bands 410 may be utilized. Each band 410 is disposed adjacent to another band 410 along a longitudinal axis LA to form a tube or cylinder. Each band 410 is a waveform formed from a plurality of struts 412 connected together by bends or crowns 414. At least one crown 414 of each band 410 is connected to a corresponding crown 414 of an adjacent band 410 by a connector 424. FIG. 14 is a close-up view of area "C" in FIG. 13 and illustrates one connector 424 connecting the crowns 414 of adjacent bands 410 to each other. At other crowns, a gap 428 is disposed between the crown 414 and the corresponding crown 414 of the adjacent bands 410, as shown in FIG. 15, which is a close-up view of area "D" in FIG. 13.

Further processing of the stent 400 may be performed after the removal of the masking plates 340. For example, and not by way of limitation, electropolishing, laser micromachining, or other processes to smooth the surfaces of the stent 400 may be performed, if necessary and or desired. Accordingly, the struts 312 and the crowns 314 of the bands 310, and the first connectors 324, of the precursor stent 300 may be slightly thicker than the final desired thickness of these elements to account for processes to smooth or otherwise finish the stent since such processes may be subtractive processes. Further, processes to remove the stilts 330, if used, or other materials between the first band 310a and the substrate 212 may also be performed. Other finishing processes may be performed on the stent 400 to prepare the stent 400 for use in a body, such as, but not limited to, passivation and sterilization. Further processing may also include steps such as adding coatings to the stent, adding radiopaque markers, adding biologically or pharmaceutically active substances to the stent, and/or adding surface features (such as recesses) to the stent. Some of this described further processing may be performed on the precursor stent 300 prior to removal of the removable masking plates 340. Further, some of the described further processing may be included in steps of forming the precursor stent. For example, and not by way of limitation, surface features such as recesses may be formed in the stent as part of the additive manufacturing process.

While the embodiments shown and described herein refer to a crown connected to a corresponding crown of an adjacent band on the precursor stent by a connector, other connections between adjacent bands may be utilized. For example, and not by way of limitation, a crown of one band may be connected to a strut of an adjacent band, or struts of adjacent bands may be connected. Further, the connectors may be angled with respect to the longitudinal axis LA or may be curved.

FIGS. 3-12 show a particular embodiment of the precursor stent 300. However, different precursor stents may be formed using additive manufacturing. For example, and not by way of limitation, additional connectors may be utilized, the bands may be slanted, different bands may have different features (such as different thicknesses), additional features such as surface features, notches, etc. may be added, and other stent design differences may be utilized which are capable of being made using additive manufacturing.

Although the embodiments shown and described herein refer to a precursor stent with bands, at least one connector and at least one removable masking plate processed to form a stent, this is not meant to limit the method, and other medical devices may be manufactured utilizing the method described herein. More specifically, a precursor medical device may include a first portion coupled to a second portion by at least one connector and a removable masking plate disposed between the first portion and the second portion. The precursor medical device may be processed to remove the masking plate, thereby forming a medical device including a first portion coupled to a second portion by at least one connector.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of making a medical device using additive manufacturing comprising the steps of:
    forming a plurality of layers of a first portion of the medical device using additive manufacturing;
    placing a first removable masking plate over the first portion, wherein the first removable masking plate includes at least one opening aligned with a point of the first portion;
    forming at least one layer of a first connector on the first portion using additive manufacturing, wherein the first connector is formed in the at least one opening of the first removable masking plate;
    forming a plurality of layers of a second portion of the medical device, wherein a first layer of the plurality of layers of the second portion is formed partially on the first connector and partially on the first removable masking plate; and
    removing the first removable masking plate without adversely affecting the first portion, the second portion, and the first connector.

2. The method of claim 1, wherein the step of removing the first removable masking plate comprises a process selected from the group consisting of physical removal, chemical etching, wet chemical dissolution, solubilization, sublimation, and melting.

3. The method of claim 1, wherein the medical device is made from a first material, the first removable masking plate is made from a second material different than the first material, and the step of removing the first removable masking plate comprises removing the second material without adversely affecting the first material.

4. The method of claim 3, wherein the first material is selected from the group consisting of cobalt-chromium alloys, cobalt-nickel-chromium alloys, nickel-titanium alloys, and molybdenum bearing stainless steel alloys.

5. The method of claim 4, wherein the second material is at least one of zinc, copper, or iron, and wherein the step of removing the first removable masking plate comprises exposing the medical device and the first removable masking plate to a neutral to acidic solution.

6. The method of claim 4, wherein the second material is at least one of lead, silver, or polyether ether ketone (PEEK), and wherein the step of removing the first removable masking plate comprises exposing the medical device and the first removable masking plate to nitric acid.

7. The method of claim 4, wherein the second material is at least one of copper, polyether ether ketone (PEEK), or copper coated calcium carbonate, and wherein the step of removing the first removable masking plate comprises exposing the medical device and the first removable masking plate to sulfuric acid.

8. The method of claim 4, wherein the second material is at least one of aluminum or aluminum oxide, and wherein the step of removing the first removable masking plate comprises exposing the medical device and the first removable masking plate to a basic solution.

9. The method of claim 8, wherein the basic solution is sodium hydroxide (NaOH) or ammonia ($NH_3$).

10. The method of claim 4, wherein the second material is polyetherimide, and wherein the step of removing the first removable masking plate comprises exposing the medical device and the first removable masking plate to at least one of chloroform, methylethylketone, methylene chloride, trichloroethane, or trichloroethylene.

11. The method of claim 4, wherein the second material is at least one of calcium carbonate or hydroxyapatite, and wherein the step of removing the first removable masking plate comprises exposing the medical device and the first removable masking plate to an acidic solution.

12. The method of claim 4, wherein the second material is selected from at least one of tin, lead, magnesium, zinc, aluminum, polyether ether ketone (PEEK) or polyetherimide, and wherein the step of removing the first removable masking plate comprises exposing the medical device and the first removable masking plate to a temperature above a melting point of the second material and below a melting point of the first material to melt the first removable masking plate.

13. The method of claim 4, wherein the second material is selected from at least one of tin, lead, magnesium, or aluminum, and wherein the step of removing the first removable masking plate comprises exposing the medical device and the first removable masking plate to a temperature and pressure such that the temperature is above the vapor equilibrium point of the second material for the pressure.

14. The method of claim 3, wherein the first material is selected from the group consisting of cobalt-chromium alloys, cobalt-nickel-chromium alloys, and molybdenum bearing stainless steel alloys.

15. The method of claim 14, wherein the second material is at least one of tantalum, molybdenum, tungsten, titanium, or silicon carbide, and wherein the step of removing the first removable masking plate comprises exposing the medical device and the first removable masking plate to xenon di-fluoride.

16. The method of claim 14, wherein the second material is magnesium, and wherein the step of removing the first removable masking plate comprises exposing the medical device and the first removable masking plate to a temperature above approximately 473° C. or to an aqueous or acidic solution with a positive potential applied to the medical device and the first removable masking plate.

17. The method of claim 14, wherein the second material is titanium diboride or zirconium diboride, and wherein the step of removing the first removable masking plate comprises exposing the medical device and the first removable masking plate to chlorine or fluorine plasma.

18. The method of claim 14, wherein the second material is Yytria stabilized zirconia, and wherein the step of removing the first removable masking plate comprises exposing the medical device and the first removable masking plate to hydrogen fluoride.

19. The method of claim 14, wherein the second material is silicon carbide, and wherein the step of removing the first removable masking plate comprises exposing the medical device and the first removable masking plate to chlorine trifluoride gas or hydrogen fluoride and nitric acid.

20. The method of claim 1, wherein the first removable masking plate includes a plurality of openings such that a plurality of connectors are formed between the first portion and the second portion.

21. The method of claim 1, further comprising the steps of:
    placing a second removable masking plate over the second portion, wherein the second removable masking plate includes at least one opening aligned with a corresponding point of the second portion; and
    forming at least one layer of a second connector on the second portion, wherein the second connector is formed in the at least one opening of the second removable masking plate;
    forming a plurality of layers of a third portion of the medical device, wherein a first layer of the plurality of layers of the third portion is formed partially on the second connector and partially on the second removable masking plate
    wherein the step of removing the first removable masking plate comprises removing the first removable masking plate and the second removable masking plate.

22. The method of claim 1, wherein the medical device is a stent.

23. The method of claim 22, wherein the first portion and the second portion each include a plurality of struts connected by a plurality crowns, and wherein the at least one opening of the first removable masking plate is aligned with corresponding crowns of the first portion and the second portion.

* * * * *